(12) United States Patent
Nelson, III et al.

(10) Patent No.: US 8,480,598 B2
(45) Date of Patent: Jul. 9, 2013

(54) GUIDE WIRE WITH SOLDERED MULTILAYER COIL MEMBER

(75) Inventors: John J. Nelson, III, Carlsbad, CA (US); David H. Burkett, Temecula, CA (US); Wayne E. Cornish, Fallbrook, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 291 days.

(21) Appl. No.: 12/881,456

(22) Filed: Sep. 14, 2010

(65) Prior Publication Data

US 2012/0065623 A1    Mar. 15, 2012

(51) Int. Cl.
*A61M 25/09* (2006.01)

(52) U.S. Cl.
USPC .......................................... 600/585; 600/434

(58) Field of Classification Search
USPC .......................................... 600/433–434, 585
See application file for complete search history.

(56) References Cited

U.S. PATENT DOCUMENTS

| | | | |
|---|---|---|---|
| 5,666,969 A * | 9/1997 | Urick et al. | 600/585 |
| 5,706,826 A | 1/1998 | Schwager | |
| 6,001,068 A | 12/1999 | Uchino et al. | |
| 6,348,041 B1 | 2/2002 | Klint | |
| 6,383,146 B1 | 5/2002 | Klint | |
| 6,502,606 B2 * | 1/2003 | Klint | 140/71 R |
| 7,715,903 B2 | 5/2010 | Hartley et al. | |
| 2007/0299366 A1 * | 12/2007 | Sharrow et al. | 600/585 |
| 2008/0161726 A1 | 7/2008 | Itou | |
| 2008/0161727 A1 | 7/2008 | Aimi et al. | |
| 2009/0163833 A1 | 6/2009 | Kinoshita et al. | |

* cited by examiner

*Primary Examiner* — Brian Szmal
*Assistant Examiner* — Emily Lloyd
(74) *Attorney, Agent, or Firm* — Fulwider Patton LLP

(57) ABSTRACT

A guide wire includes an elongate core section and a flexible member disposed on the distal end, the flexible member including a first wire wound into an inner helical coil in a first direction and a second wire wound into an outer helical coil wrapped about the first helical coil in the opposite direction. The two combined helical coils add stiffness and torque transmission to the guide wire without sacrificing tactile feedback.

10 Claims, 4 Drawing Sheets

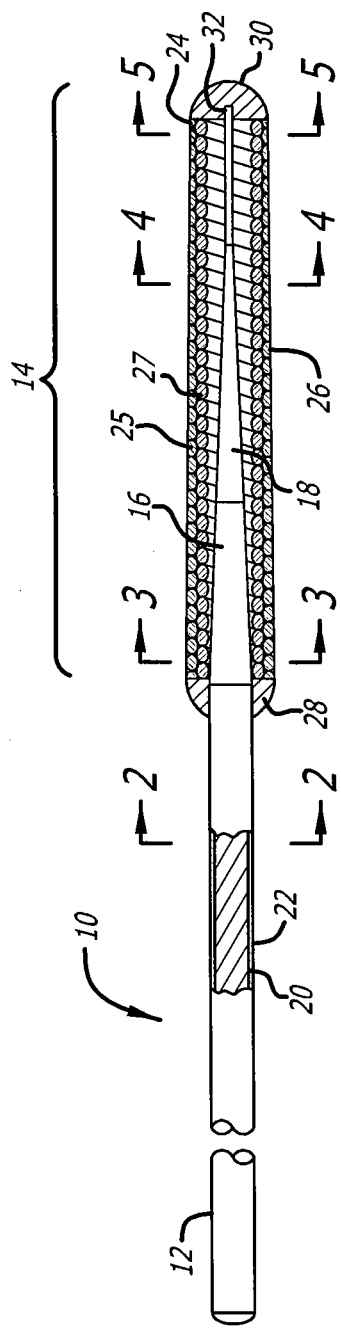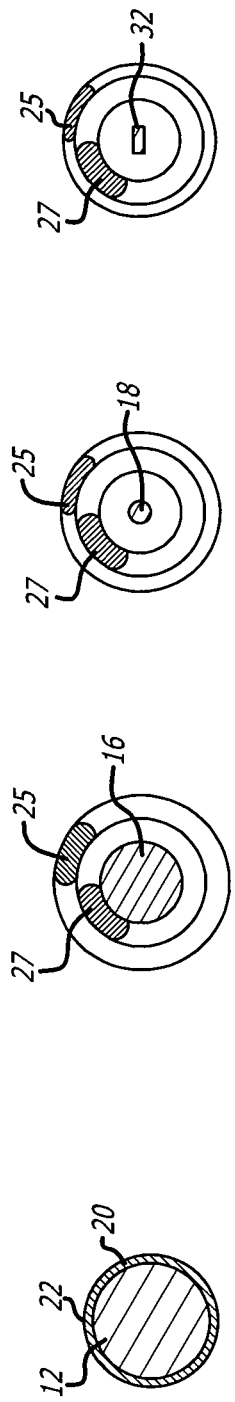
FIG. 1
FIG. 2
FIG. 3
FIG. 4
FIG. 5

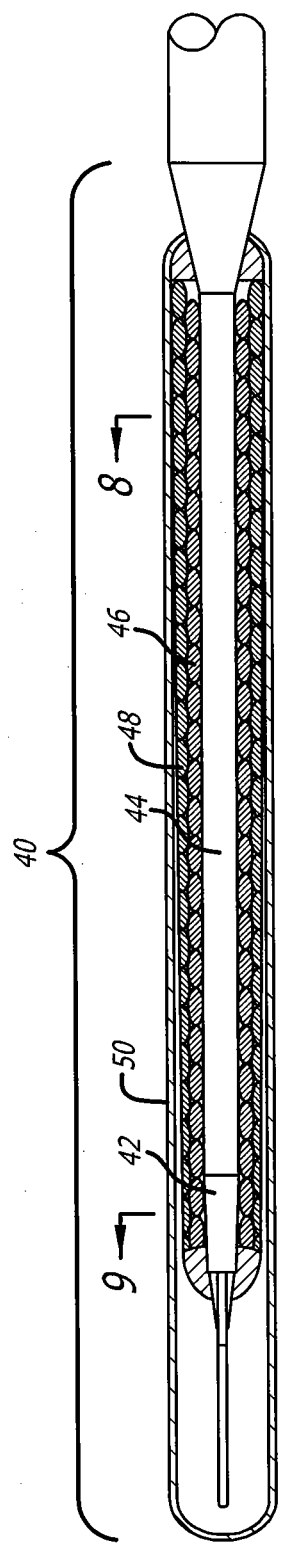
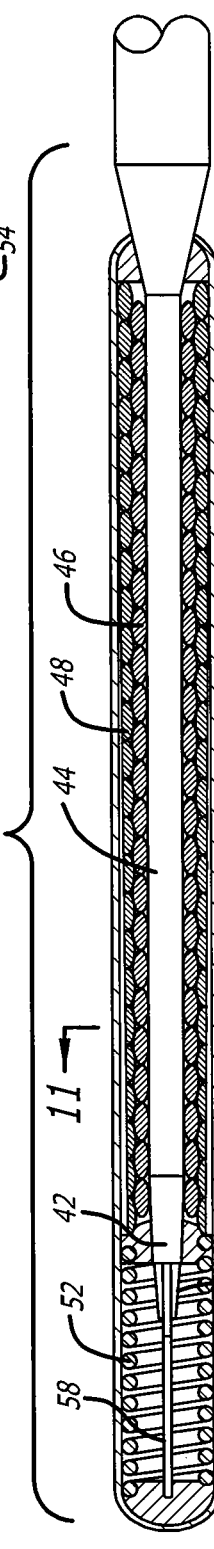
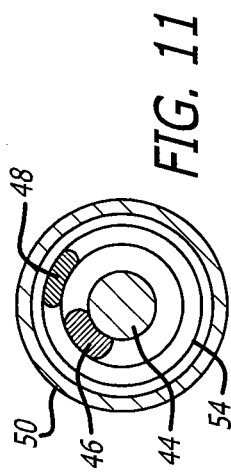

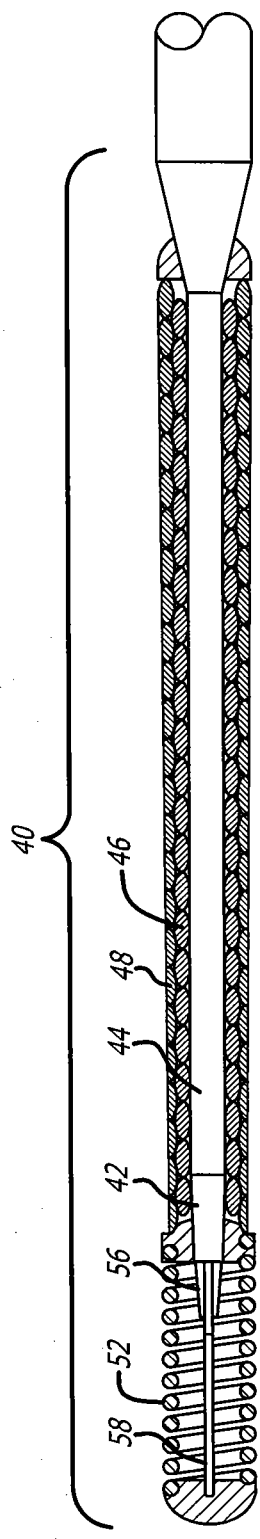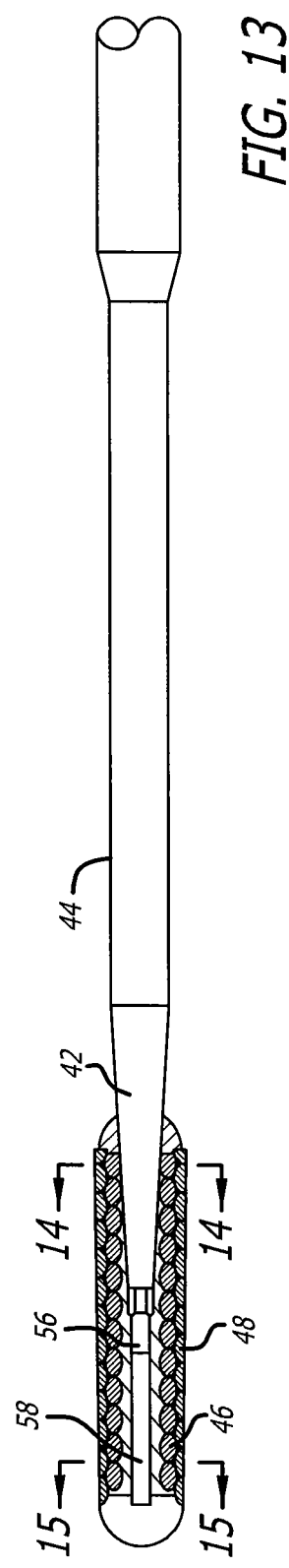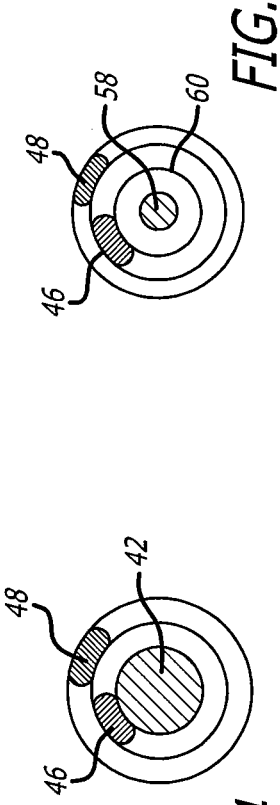

GUIDE WIRE WITH SOLDERED MULTILAYER COIL MEMBER

BACKGROUND

This invention relates to the field of guide wires for advancing intraluminal devices such as stent delivery catheters, balloon dilatation catheters, atherectomy catheters and the like within a patient's body, such as within a patient's vasculature.

In a typical percutaneous procedure in a patient's coronary system, a guiding catheter having a preformed distal tip is percutaneously introduced into a patient's peripheral artery, e.g. femoral, radial or brachial artery, by means of a conventional Seldinger technique and advanced therein until the distal tip of the guiding catheter is seated in the ostium of a desired coronary artery. There are two basic techniques for advancing a guide wire into the desired location within the patient's coronary anatomy, the first is a preload technique which is used primarily for over-the-wire (OTW) devices and the bare wire technique which is used primarily for rail type systems. With the preload technique, a guide wire is positioned within an inner lumen of an OTW device such as a dilatation catheter or stent delivery catheter with the distal tip of the guide wire just proximal to the distal tip of the catheter and then both are advanced through the guiding catheter to the distal end thereof The guide wire is first advanced out of the distal end of the guiding catheter into the patient's coronary vasculature until the distal end of the guide wire crosses the arterial location where the interventional procedure is to be performed, e.g. a lesion to be dilated or a dilated region where a stent is to be deployed.

The catheter, which is slidably mounted onto the guide wire, is advanced out of the guiding catheter into the patient's coronary anatomy over the previously introduced guide wire until the operative portion of the intravascular device, e.g. the balloon of a dilatation or a stent delivery catheter, is positioned across the arterial location. Once the catheter is in position with the operative means located within the desired arterial location, the interventional procedure is performed. The catheter can then be removed from the patient over the guide wire. Usually, the guide wire is left in place for a period of time after the procedure is completed to ensure re-access to the arterial location if it is necessary. For example, in the event of arterial blockage due to dissected lining collapse, a rapid exchange type perfusion balloon catheter such as described and claimed in U.S. Pat. No. 5,516,336 (McInnes et al.), can be advanced over the in-place guide wire so that the balloon can be inflated to open up the arterial passageway and allow blood to perfuse through the distal section of the catheter to a distal location until the dissection is reattached to the arterial wall by natural healing.

With the bare wire technique, the guide wire is first advanced by itself through the guiding catheter until the distal tip of the guide wire extends beyond the arterial location where the procedure is to be performed. Then a rail type catheter, such as described in U.S. Pat. No. 5,061,273 (Yock) and the previously discussed McInnes et al. which are incorporated herein by reference, is mounted onto the proximal portion of the guide wire that extends out of the proximal end of the guiding catheter outside of the patient. The catheter is advanced over the guide wire, while the position of the guide wire is fixed, until the operative means on the rail type catheter is disposed within the arterial location where the procedure is to be performed. After the procedure the intravascular device may be withdrawn from the patient over the guide wire or the guide wire advanced further within the coronary anatomy for an additional procedure.

Conventional guide wires for angioplasty, stent delivery, atherectomy and other vascular procedures usually comprise an elongated core member with one or more tapered sections near the distal end thereof and a flexible body such as a helical coil or a tubular body of polymeric material disposed about the distal portion of the core member. A shapeable member, which may be the distal extremity of the core member or a separate shaping ribbon secured to the distal extremity of the core member, extends through the flexible body and is secured to the distal end of the flexible body by soldering, brazing or welding which forms a rounded distal tip. Torquing means are provided on the proximal end of the core member to rotate, and thereby steer, the guide wire while it is being advanced through a patient's vascular system.

Further details of guide wires, and devices associated therewith for various interventional procedures can be found in U.S. Pat. No. 4,748,986 (Morrison et al.); U.S. Pat. No. 4,538,622 (Samson et al.): U.S. Pat. No. 5,135,503 (Abrams); U.S. Pat. No. 5,341,818 (Abrams et al.); U.S. Pat. No. 5,345,945 (Hodgson, et al.) and U.S. Pat. No. 5,636,641 (Fariabi) which are hereby incorporated herein in their entirety by reference thereto.

One of the difficulties with conventional coil guide wires is that it is difficult to transmit torque at the distal end of the guide wire. When a conventional coil has a torque applied, depending upon the direction of the torque the coil can either expand or contract, but only a percentage of the torque is transmitted to the end of the coil. In the course of navigating the guide wire through the patient's vascular and in some procedures it is necessary to apply a torque at the proximal end of the guide wire to effect a torque at the distal end. With conventional coils this can sometimes be difficult. The present invention seeks to address this situation by providing a guide wire with flexibility and stiffness characteristics that are equal or superior to the existing coil guide wires but also transmit torque in a more consistent and reliable manner.

SUMMARY OF THE INVENTION

A guide wire of the present invention has a flexible coil section that is fashioned from a tube made of helically wound strands of metal such as stainless steel wire forming a first layer that is soldered to a wire coil serving as a second layer, where the multi-layer construction of the inner and outer layers leaves open a hollow center channel for insertion of a core member. In one preferred embodiment of the present invention, the multi-layer flexible coil section is mechanically ground down to either a constant or tapered outer diameter by removing selected material from the flexible coil section for desired stiffness and flexibility. The result is a guide wire that has a variable diameter flexible coil section at the distal section of the guide wire for improved pushability, torque transmission, and tactile response.

BRIEF DESCRIPTION OF THE DRAWINGS

FIG. 1 is an elevational view partially in section of a guide wire embodying features of the invention.

FIG. 2 is a cross-sectional view of the guide wire shown in FIG. 1 taken along lines 2-2.

FIG. 3 is a cross-sectional view of the guide wire shown in FIG. 1 taken along lines 3-3.

FIG. 4 is a cross-sectional view of the guide wire shown in FIG. 1 taken along lines 4-4.

FIG. 5 is a cross-sectional view of the guide wire shown in FIG. 1 taken along lines 5-5.

FIG. 7 is a sectional view of another embodiment of the present invention.

FIG. 8 is a cross-sectional view of the embodiment of FIG. 7 taken along lines 8-8.

FIG. 9 is a cross-sectional view of the embodiment of FIG. 7 taken along lines 9-9.

FIG. 10 is a sectional view of another embodiment of the present invention.

FIG. 11 is a cross-sectional view of the embodiment of FIG. 10 taken along lines 11-11.

FIG. 12 is a sectional view of another embodiment of the present invention.

FIG. 13 is a sectional view of yet another embodiment of the present invention.

FIG. 14 is a cross-sectional view of the embodiment of FIG. 13 taken along lines 14-14.

FIG. 15 is a cross-sectional view of the embodiment of FIG. 13 taken along lines 15-15.

DETAILED DESCRIPTION OF THE PREFERRED EMBODIMENTS

Figure 6:
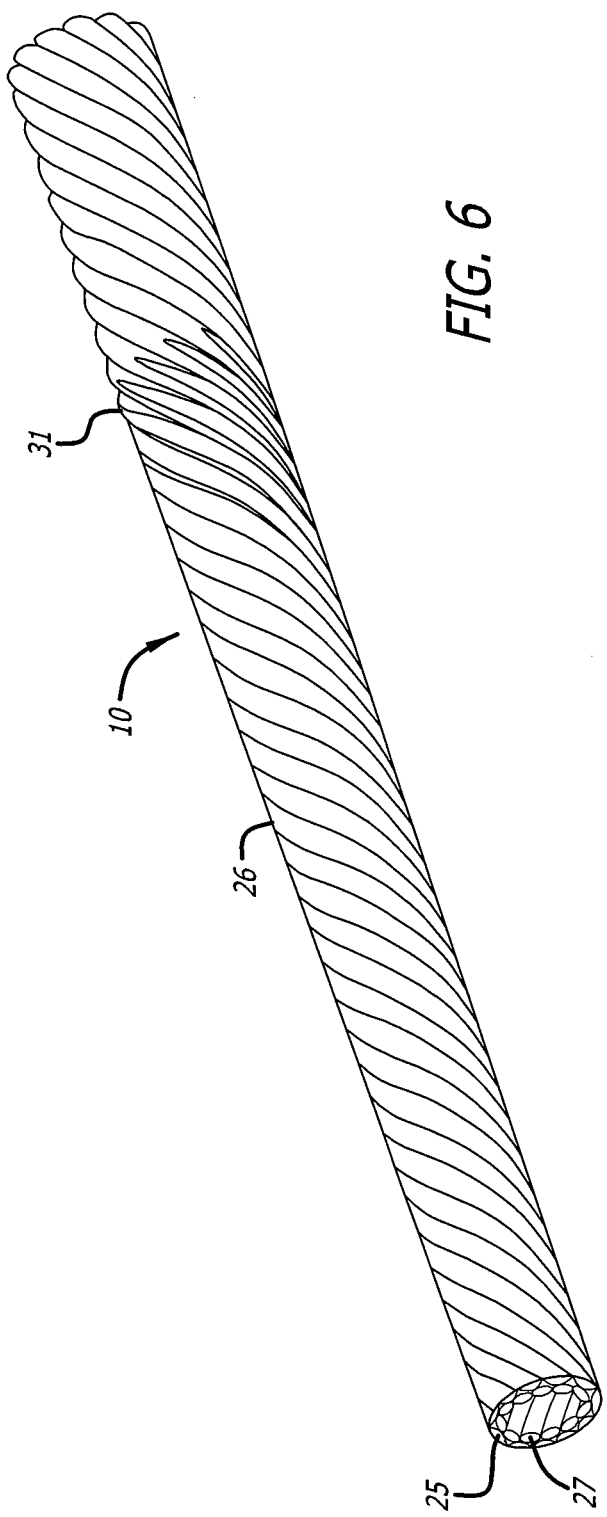
FIG. 6 is an elevated perspective view of an embodiment of the guide wire of the present invention having a tapered distal end.

A guide wire typically includes a flexible wire positioned in an organ, vessel, or duct of a patient for the purpose of directing passage of a larger device threaded over or along the length of the guide wire to a desired location in the vasculature of the patient. A wide variety of guide wires have been developed for various applications including medical applications, such as, but not limited to, coronary angioplasty. Also, endovascular interventions are rapidly advancing as a viable alternative for invasive vascular surgery. During these interventions, a guide wire is generally inserted into a region of a patient, such as the groin region, and the guide wire is then advanced to a desired location, typically under fluoroscopic guidance. Accurate positioning of the guide wire with respect to the vasculature is a prerequisite for a successful procedure. Furthermore, during neuro-interventions, positioning the guide wire accurately is difficult due to the complexity of the vasculature and narrowness of the blood vessels, thereby resulting in an increase of intervention time and exposure to radiation.

The present invention is directed to an elongated intracorporeal device such as a guide wire constructed of a hollow helical strand about a core coil. Hollow helical strand wires are available, for example, by Fort Wayne Metals of Fort Wayne, Indiana. The outer layer of the hollow helical strand comprises multiple strands of metal wire such as stainless steel, Nitinol, or the like which is soldered to an inner core wire coil. The construction provides better torque transmission while maintaining or improving tactile feedback and maintains a constant diameter under the influence of applied torque.

FIG. 1 is a side elevational view partially in section of one embodiment of the present invention guide wire 10. The guide wire 10 includes an elongated core having a proximal core section 12 and a distal core section 14. In this embodiment, the entire wire core is made from a single material such as stainless steel. In various alternative embodiments (not shown), the proximal core section can be made from a high strength steel while the distal core section 14 is made from a superelastic alloy such as nickel-titanium (e.g., Nitinol) or the like. The two core sections 12, 14 can be joined by a weld or adhesive, and/or by an interconnecting hypotube made from various materials.

Returning to FIG. 1, the guide wire 10 includes optional tapered sections 16, 18. Specifically, the present invention contemplates one or more tapered profiles at varying degrees of taper, although straight, curved, and/or stepped profiles are also contemplated. The guide wire 10 further includes a coating 20 disposed on and adhering to the wire core 22. The surface coating 20 or the surface of the wire core 22, or both, include color coding as discussed below.

The surface coating 20 may only partially cover the guide wire core 22 or may envelope the entire core altogether. The surface coating may be a low friction material such as polytetrafluoroethylene ("PTFE") that aids in positioning the guide wire 10. The coating may include positional markers at the distal or proximal end to aid the practitioner in locating the end portion(s) of the guide wire 10. Toward the distal end 24 of the guide wire 10 is typically a flexible member 26. Preferably the flexible member 26 is one or more helical coils 25,27 welded, bonded, soldered, or otherwise attached to the distal core section 14. In a preferred embodiment, the flexible member is made of a radiopaque material such as platinum to help provide accurate positioning of the guide wire. In the embodiment shown, the flexible member 26 is attached at its proximal end by a weld or solder mass 28 and at its distal end by a solder ball 30 or similar rounded tip. Furthermore, the guide wire 10 features a flattened distal tip 32 that extends into the solder ball 30. FIGS. 2, 3, and 4 are cross-sectional views of the guide wire 10 taken along lines 2-2, 3-3, and 4-4 of FIG. 1, respectively.

The combination of coils 25 and 27, wound in opposite directions, provide the guide wire with a tip section that is both flexible and possesses enhanced torque capabilities. The distal tip will not easily coil (or uncoil) when a torque is applied at the proximal end due to the dual nature of the helical coils 25, 27. The present invention has been found to enjoy good torque transmission while maintaining good tactile feedback for guide wires of similar diameters. This is because torque applied in the direction of one of the helical coils will be resisted by the second helical coil, maintaining more of the original torque. By advantageously shaving or tapering the diameter of the guide wire's core or the outer helical coil in the distal direction, the stiffness properties can be modified to the needs of the application.

FIG. 6 illustrates the flexible member 26 with first and second helical coils 25, 27 without the core section, where the outer helical coil 27 has been tapered by shaving the surface beginning at a location 31. It is to be understood that the tapering of the flexible member can occur at any suitable location to modify the stiffness of the guide wire and that the depicted taper is merely exemplary.

A second embodiment of the present invention is shown in a sectional view in FIG. 7. In this embodiment, a distal core section 40 narrows to a first tapered section 42, which supports a constant diameter internal member 44. Wrapped around the internal member 44 is a first helical coil 46 wound in a first direction, and a second helical coil 48 wrapped around the first helical coil but in the opposite direction. The outer helical coil 48 is tapered in the distal direction so as to effect a reduced stiffness in this direction. A polymer coating 50 surrounds the helical coils. FIGS. 8 and 9 illustrate cross-sectional views of the guide wire along lines 8-8 and 9-9.

FIG. 10 illustrates another embodiment of the present invention, which is similar to the embodiment of FIG. 7 but includes a helical coil tip 52 about the distal end of the internal core member 44. FIG. 11 shows a cross-sectional view where coil 46 is wrapped around core 44, and coil 48 is wrapped around coil 46, and a gap 54 exists between the polymer coating and the outer helical coil due to the tapering of the outer helical coil 48. FIG. 12 is yet another embodiment of the present invention and comprises the embodiment of FIG. 10 without the plastic coating.

FIG. 13 is yet another embodiment of the present invention, where the guide wire has a double helical coil positioned at the distal tip of the core 44. The core 44 has a first tapered section 42 and a second tapered section 56, which narrows to a constant diameter end section 58. The constant diameter end section 58 has a first inner helical coil 46 wrapped around it, and a second outer helical coil 48 is wrapped around the first inner helical coil 46. The second outer helical coil 48 is tapered in a distal direction to modify the stiffness in that direction, and the helical coils can also include a polymer coating such as that shown in FIG. 7. FIGS. 14 and 15 illustrate cross sectional views, where a gap 60 is present in FIG. 15 due to the narrowing of the end section 58 from the tapered section 56.

It is to be understood that the foregoing description is intended to be illustrative of embodiments of the present invention but is not intended to be limiting in any manner. One of ordinary skill in the art will readily appreciate modifications and alterations to the above described examples, and the intention includes all such modifications and alterations. Accordingly, the scope of the invention is properly interpreted to be encompassed by the words of the appended claims, using the words' ordinary meaning, without limiting the definition of those words to the examples provided herein.

What is claimed:

1. A guide wire for use in a medical procedure, comprising:
   an elongate core member having a proximal end and a distal end, the distal end including a first tapered portion narrowing in the distal direction;
   a flexible member disposed on the elongate core at the distal end, the flexible member comprising a first wire wound into an inner hollow helical coil in a first direction about the tapered portion of the elongate core member and a second wire wound into an outer helical coil in a second direction about the inner helical coil; and
   the flexible member has a polymer coating and a tapering of the outer helical coil results in a gap between the outer helical coil and the polymer coating.

2. The guide wire of claim 1, wherein the outer helical coil is ground to the taper, the taper narrowing in the distal direction, and wherein the inner hollow helical coil does not have a taper.

3. The guide wire of claim 1, wherein the elongate core member has a second tapered portion adjacent the first tapered portion.

4. The guide wire of claim 1, wherein the elongate core member includes a coating.

5. The guide wire of claim 1, further comprising a third helical coil member spaced distally from the flexible member, the third helical coil member coupled to the elongate core member.

6. The guide wire of claim 5, wherein the third helical coil member is enclosed in the polymer coating.

7. A guide wire for use in a medical procedure, comprising:
   an elongate core member having a proximal end and a distal end;
   a flexible member disposed on the elongate core at the distal end, the flexible member comprising a first wire wound into an inner helical coil in a first direction about a tapered portion of the elongate core member and a second wire wound into an outer helical coil in a second direction about the inner helical coil, the flexible member coupled to the elongate core member via solder attachments at first and second ends of the flexible member; and
   the flexible member has a polymer coating and a tapering of the outer helical coil results in a gap between the outer helical coil and the polymer coating.

8. The guide wire of claim 7, wherein the outer helical coil is ground to the taper, the taper narrowing in the distal direction, but the inner helical coil does not have a taper.

9. The guide wire of claim 7, wherein the elongate core member includes a coating.

10. The guide wire of claim 7, wherein the inner helical coil is hollow.

* * * * *